(12) United States Patent
Iwasaki et al.

(10) Patent No.: US 7,067,823 B2
(45) Date of Patent: Jun. 27, 2006

(54) MICRO-SAMPLE PICK-UP APPARATUS AND MICRO-SAMPLE PICK-UP METHOD

(75) Inventors: Kouji Iwasaki, Chiba (JP); Yo Yamamoto, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/839,508

(22) Filed: May 5, 2004

(65) Prior Publication Data

US 2004/0246465 A1     Dec. 9, 2004

(30) Foreign Application Priority Data

May 6, 2003   (JP)   .............................. 2003-127885
Apr. 26, 2004 (JP)   .............................. 2004-129376

(51) Int. Cl.
   *G01N 1/00*    (2006.01)
(52) U.S. Cl. ........................... 250/442.11; 250/559.27; 250/310; 250/311
(58) Field of Classification Search ........... 250/442.11, 250/559.27, 310, 311
   See application file for complete search history.

(56) References Cited

U.S. PATENT DOCUMENTS 6,420,722 B1 *  7/2002  Moore et al. .......... 250/559.27
6,781,125 B1 *  8/2004  Tokuda et al. .............. 250/310

\* cited by examiner

*Primary Examiner*—Nikita Wells
*Assistant Examiner*—Zia R. Hashmi
(74) *Attorney, Agent, or Firm*—Adams & Wilks

(57) ABSTRACT

A micro-sample pick-up apparatus has a probe for picking up a micro sample, a probe holder for holding the probe, an XYZ driver mechanism for moving the probe holder in the three-dimensional directions of X, Y and Z, and an observation mechanism for observing the sample and the probe. A low-vibration rotary mechanism disposed in the probe holder for rotating the probe about an axis of the probe.

19 Claims, 6 Drawing Sheets

FIG. 2A
FIG. 2B
FIG. 2C
FIG. 2D
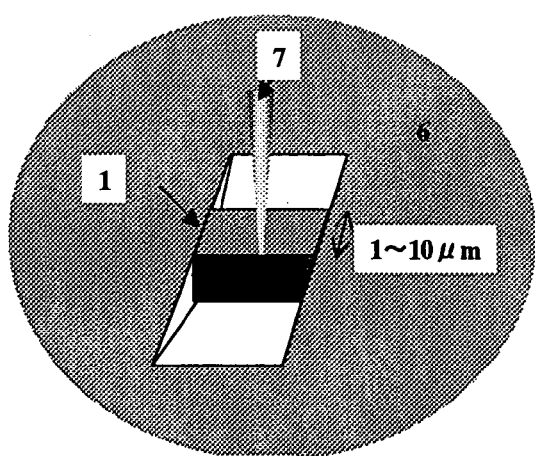
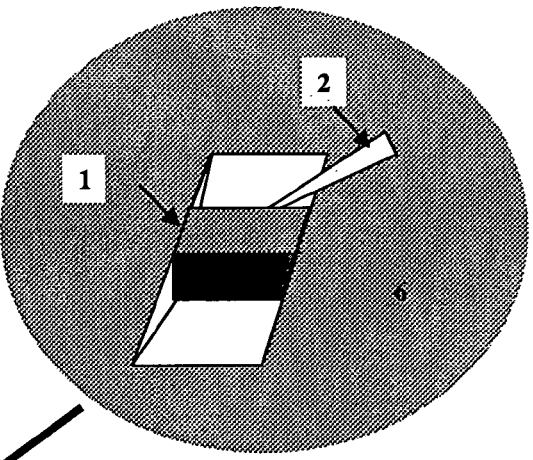
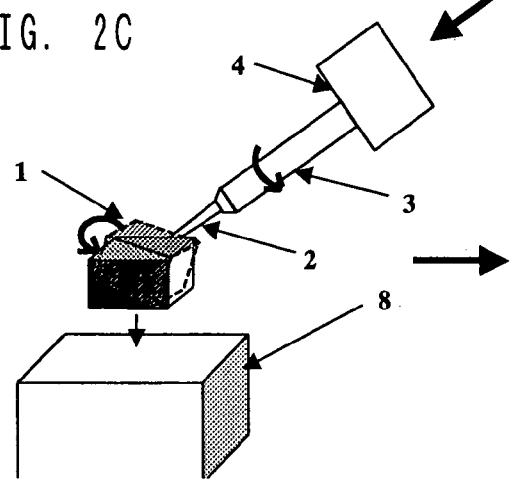
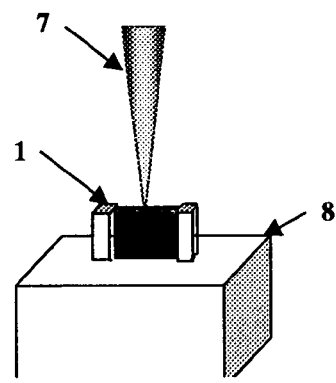

FIG. 3A
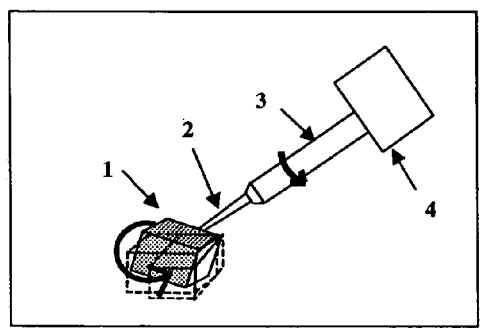
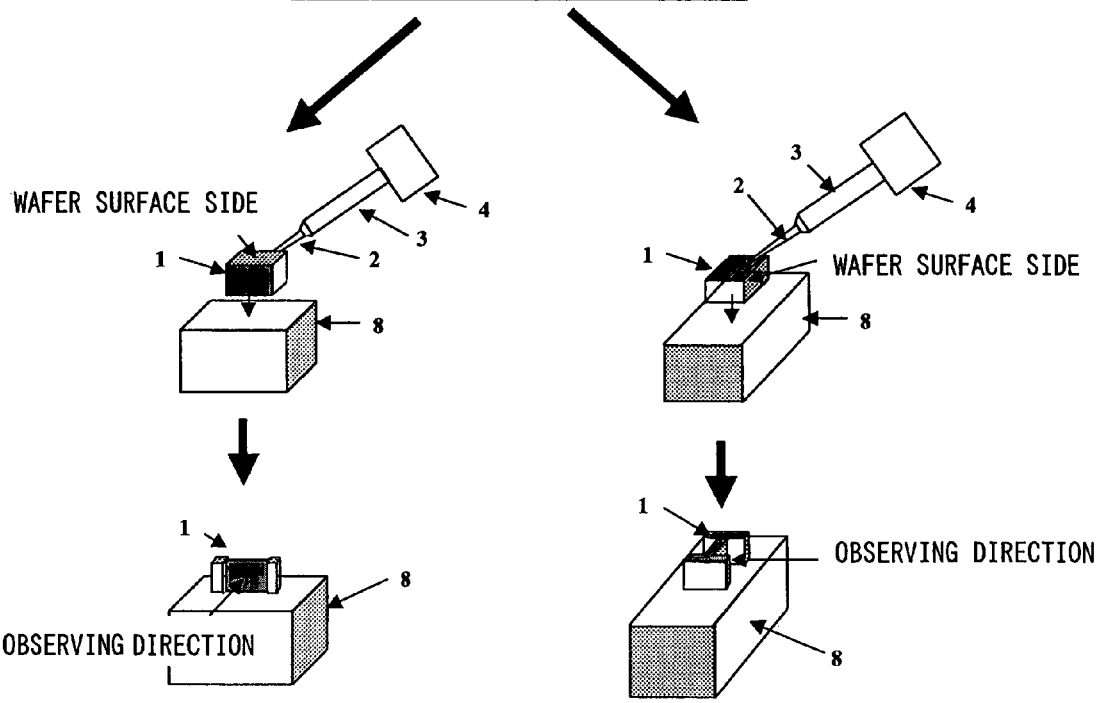
FIG. 3B          FIG. 3C

FIG. 4A
FIG. 4B
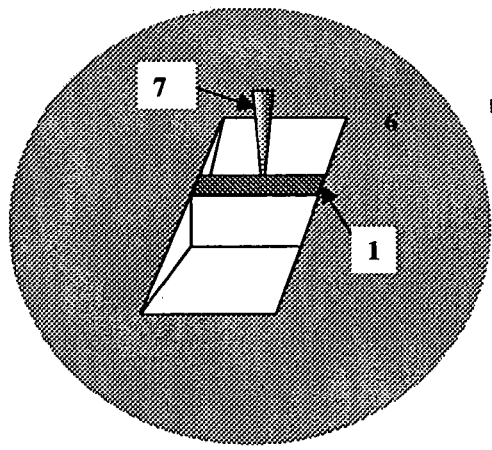
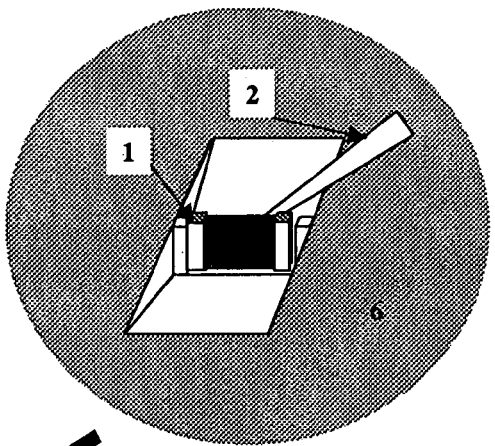
FIG. 4C
FIG. 4D
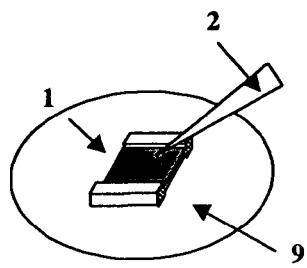
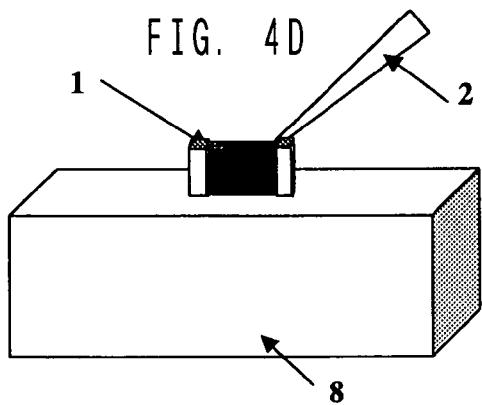

MICRO-SAMPLE PICK-UP APPARATUS AND MICRO-SAMPLE PICK-UP METHOD

BACKGROUND OF THE INVENTION

1. Field of the Invention

The present invention relates to a micro-sample pick-up apparatus used for picking up a micro sample for an electron microscope or the like, the micro sample being cut out with a charged particle beam or the like.

2. Description of the Related Art

Focused ion beam systems are adapted for minute scale processing of an arbitrary area. The focused ion beam systems have been widely used for preparing samples for TEM (Transmission Electron Microscope) observation or the like for detecting wafer defects produced in the course of fabrication of semiconductor devices.

As a method of preparing samples for TEM observation of a particular area of a wafer, there have conventionally been known a method called a pick-up method or a lift-out method (see, for example, Document 1). Description will hereinbelow be made on this method with reference to FIGS. 4A to 4D. First, as shown in FIG. 4A, a focused ion beam 7 is irradiated on a desired area of a wafer 6 for performing a thinning processing on an observation target area. Subsequently, as shown in FIG. 4B, the thinned portion is made to adhere to a tip of a probe 2 so as to be picked up as a micro sample 1. A microscope system equipped with a manipulator, as shown in FIG. 6, is used for picking up the micro sample. The microscope system with manipulator includes the probe 2, a probe holder 3 for holding the probe, an XYZ driver mechanism 5 for operation of the probe, and an optical microscope 11. The micro sample 1 is extremely small, having a transverse dimension of 10 to 20 μm and a longitudinal dimension on the order of 5 μm. Hence, an electrostatic force between the tip of the probe 2 and the micro sample 1 may be utilized for causing the micro sample 1 to adhere to the tip of the probe 2. The micro sample 1 is placed on an organic thin film 9 as shown in FIG. 4C. An article consisting of the micro sample 1 resting on the organic film 9 is committed to TEM observation as an observation sample. Once placed on the organic thin film 9, the thinned sample cannot be processed further. However, in a case where the thin sample thus picked up requires an additional processing (hereinafter, the lift-out method permitting the additional processing is described), the thin sample 1 is placed on a special sample stage 8 in an upright position, as shown in FIG. 4D. In this case, the placement of the micro sample requires an exact positioning. While FIG. 4D depicts the special sample stage 8 in a rectangular shape, the form of the special sample stage is not limited to the rectangular shape and various other shapes ar proposed (see, for example, Document 2).

[Document 1]
F. A. Stevie et al., "Application of focused ion beam lift-out specimen preparation to TEM, SEM, STEM, AES, STEM, AES and SIMS analysis", Surface and Interface Analysis, 31, pp 345(2001)

[Document 2]
Daisuke, Sakata, "FIB lift-out method permitting additional processing", the gist of lectures of the 58-th session of Japan Electro-microscopy Society, Vol. 37, p247(2002)

The micro sample to be picked up is made to adhere to the probe by way of the electrostatic force between the probe and the micro sample, so that the micro sample on the probe may be oriented in any direction. Therefore, the probe is rotated in order to orient the micro sample downwardly relative to the probe before the micro sample thus picked up is placed oh the organic film. In the conventional microscope system with manipulator, as well, the probe may be rotated by an operator directly manipulating the probe holder with his hand 10. However, this may lead to a problem that the micro sample may be lost because of vibrations associated with unsteady hand movements (FIG. 5A), or that the sample may be increased in the degree of eccentricity due to displacement caused by the unsteady hand movements (FIG. 5B). Furthermore, the lift-out method permitting the additional processing requires the micro sample to be exactly positioned and besides to be precisely controlled for its orientation when the micro sample is placed on the sample stage in the upright position. Unfortunately, however, the conventional method does not offer the ability to control the orientation of the micro sample with high precisions, thus involving a potential problem of the fall of the micro sample (FIG. 5C).

The foregoing examples have been described with reference to the case where the optical microscope is used as observation means. In a case where an electron microscope or ion microscope is used as the observation means, the probe is disposed in a vacuum apparatus which does not allow for a direct access to the probe holder. Therefore, it is impossible to make adjustment on the micro sample with respect to the rotational direction.

In view of the foregoing, it is an object of the invention to provide a micro-sample pick-up apparatus and method adapted to accomplish a high-precision control of the micro sample with respect to the rotational direction, without applying vibrations to the probe holder.

SUMMARY OF THE INVENTION

For achieving the above object of the invention, a microscope system with manipulator incorporates therein a low-vibration probe rotary mechanism. The use of the rotary mechanism provides for the high-precision control of the micro sample with respect to the rotational direction without applying vibrations to the micro sample.

BRIEF DESCRIPTION OF THE DRAWINGS

FIGS. 2A–2D are explanatory diagrams showing a procedure of placing a micro sample on a special sample stage according to the embodiment of the invention;

FIGS. 3A–3C are explanatory diagrams showing how to place the micro sample on the special sample stage according to the embodiment of the invention;

FIGS. 4A–4D are explanatory diagrams showing a method of picking up the micro sample using a conventional microscope system with manipulator;

DETAILED DESCRIPTION OF THE PREFERRED EMBODIMENTS

A preferred embodiment of the invention will hereinbelow be described with reference to the accompanying drawings.

Figure 1:
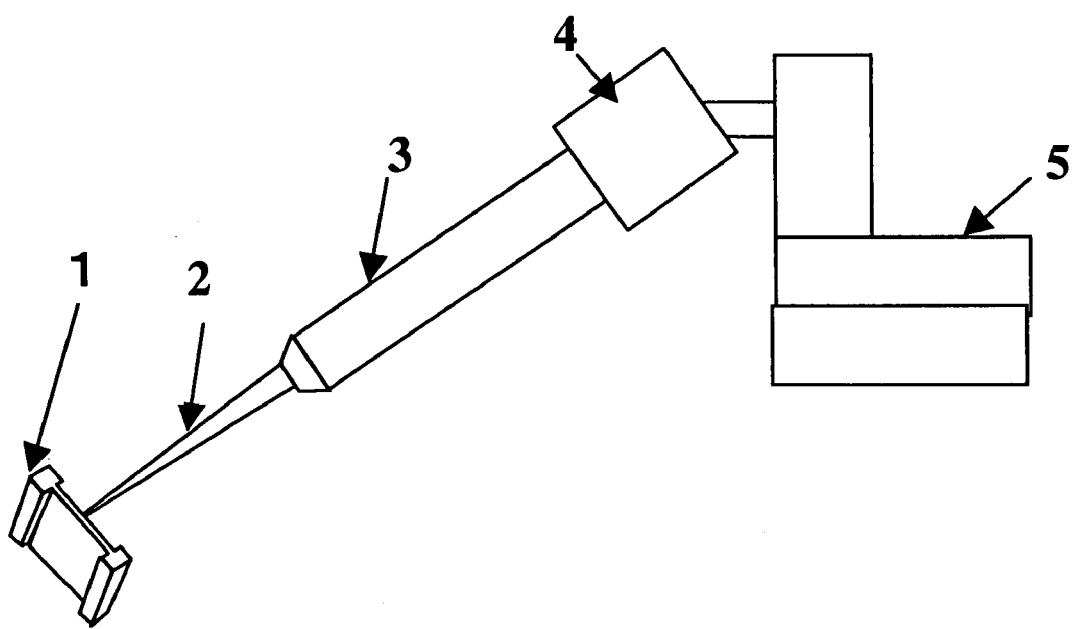
FIG. 1 is an explanatory diagram of a probe rotary mechanism employing a motor in accordance with one embodiment of the invention.
Figure 5A:
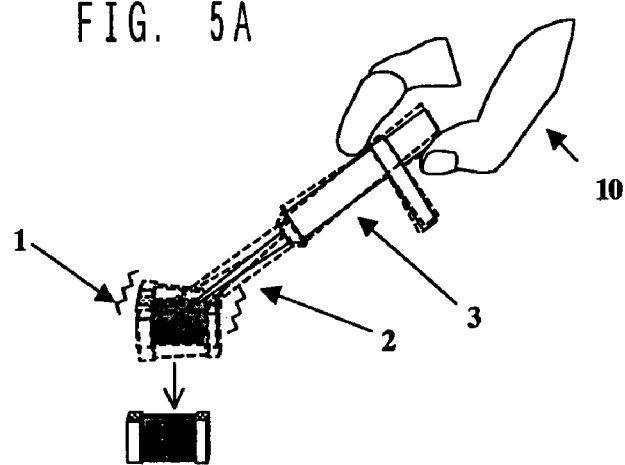
FIGS. 5A–5C are explanatory diagrams showing problems encountered by the conventional micro-sample pick-up method.
Figure 5B:
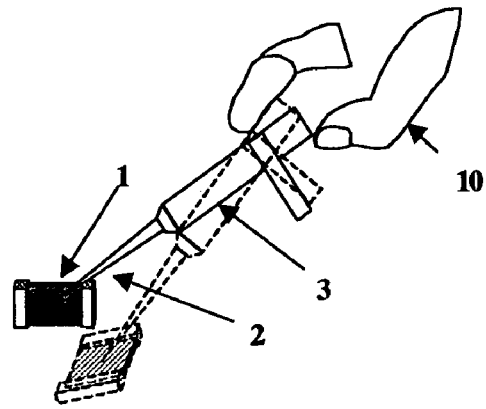
Figure 5C:
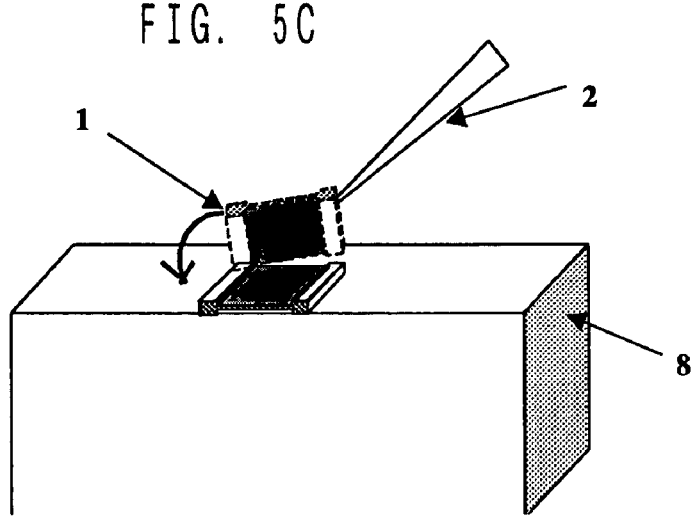
Figure 6:
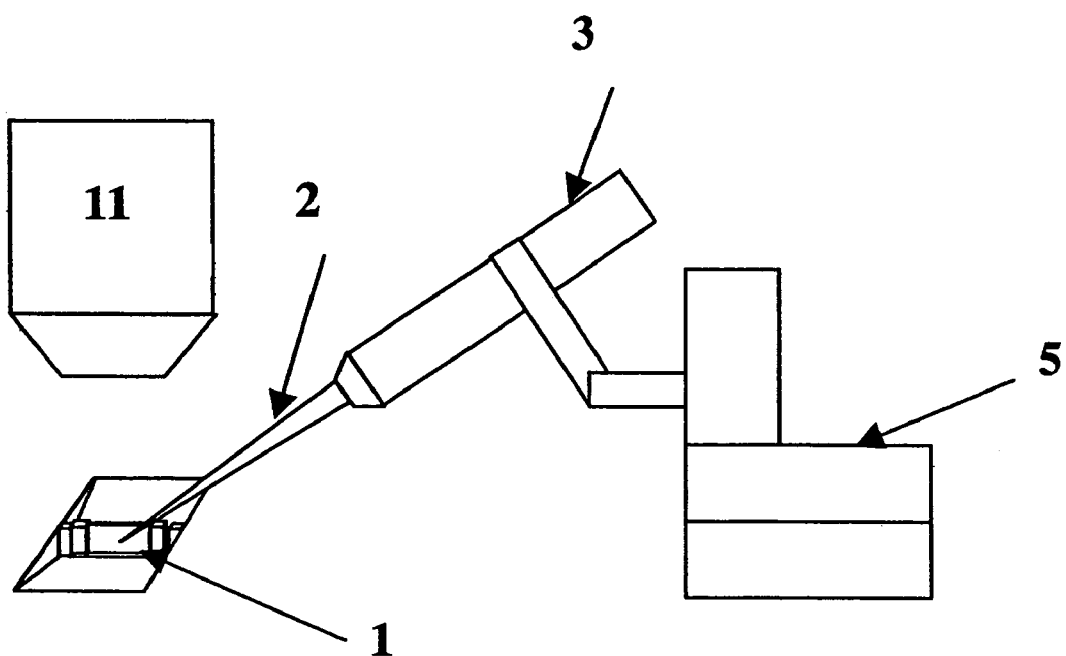
FIG. 6 is a diagram illustrating an arrangement of the conventional microscope system with manipulator.

FIG. 1 illustrates an example of a common rotary mechanism which employs a low-vibration stepping motor for rotating a probe. An XYZ driver mechanism 5 is adapted to move a support object in three dimensional directions of X, Y and Z. A low-vibration stepping motor 4 is disposed between the XYZ driver mechanism 5 and a probe holder 3 as fixed to the mechanism and the holder. The probe holder 3 is in the form of a cylinder or column and serves to hold a probe 2. The probe holder 3 is mounted to a rotary shaft of the low-vibration stepping motor 4. After a micro sample 1 is picked up by means of the probe 2, the low-vibration stepping motor 4 is rotated for bringing the whole body of the probe holder 3 into rotation. At this time, a state of a probe tip is observed with an optical microscope so that the rotation of the low-vibration stepping motor may be stopped at a point of time that the micro sample is brought into a desired orientation. As described above, the orientation of the micro sample 1 can be precisely controlled without manually manipulating the probe holder 3. Other usable observation means may include an electron microscope, ion microscope and the like. That is, the invention permits the orientation of the micro sample to be controlled without manually manipulating the probe holder and hence, the micro sample placed in a vacuum apparatus can be adjusted for its orientation while being observed with the electron microscope or ion microscope.

The description of the above example illustrates the low vibration stepping motor as a mechanism arranged to rotate the whole body of the probe holder. An alternative arrangement may be made such that the low vibration mechanism is incorporated in the probe holder so as to rotate only a tip of the probe holder. In the case where the low vibration rotary mechanism is incorporated in the probe holder, a so that the rotation of the rotatable portion may entail a decreased shift of the micro sample if the micro sample is eccentric. Thus the low vibration rotary mechanism constitutes rotary means for rotating the probe about a longitudinal axis thereof by rotating only the tip of the probe holder to thereby correct a rotational direction of the micro sample without substantially vibrating the micro sample.

FIGS. 2A–2D illustrate a micro-sample pick-up method according to an embodiment of the invention. Description is made here on the embodiment of a lift-out method permitting an additional processing. First, as shown in FIG. 2A, a focused ion beam 7 is irradiated on a desired area of a wafer for performing a thinning processing on the area defining an observation target. In this processing, the thickness of the thinned portion is normally on the order of 1 to 10 μm. Subsequently, the micro sample 1 is made to adhere to the probe 2, as shown in FIG. 2B. In order to pick up the micro sample 1, the adhesion of the micro sample to the probe is accomplished by way of an electrostatic force between the probe and the micro sample. Accordingly, the micro sample on the probe may be oriented in any direction. As shown in FIG. 2C, therefore, the rotary mechanism incorporated in the micro-sample pick-up apparatus is operated for precise control of the orientation of the micro sample while making observation of the orientation of the micro sample. The orientation control is carried out using the low-vibration rotary mechanism and hence, there is no fear of applying vibrations to the micro sample. It is thus ensured that the micro sample is prevented from being lost due to the vibrations. The micro sample thus adjusted for the orientation is placed on a special sample stage 8 for additional processing and fixed thereon, as shown in FIG. 2D. Subsequently, the micro sample is subjected to an additional processing using a charged particle beam 7.

According to the lift-out method permitting the additional processing, it is possible to change an observation surface by changing the orientation in which the micro sample is placed. FIGS. 3A–3C illustrate examples of how to change the observation surface. FIG. 3A illustrates a state of the micro-sample being rotated by the manipulator with a motor 4. In an example shown in FIG. 3B, the micro sample is picked up and then, placed in a manner to direct a surface side of a removed wafer upwardly. The charged particle beam is irradiated from above and scanned on the sample for thinning. After thinning, the observation is made along a direction orthogonal to the front side of the wafer or along a sectional direction thereof. In an example shown in FIG. 3C, the front side of the wafer is directed laterally and the sample is thinned by performing an etching processing along a direction parallel to the front side. That is, the observation is made along a planar direction. In this case, it is crucial to orient the micro sample precisely in a desired direction according to a surface to be observed. The invention is adapted to accomplish the precise control of the orientation of the micro sample by means of the rotary mechanism incorporated in the micro-sample pick-up apparatus. In this respect, the invention is highly effective in such an application.

According to the invention as described above, the microscope system with manipulator employs the micro-sample pick-up apparatus incorporating therein the low-vibration rotary mechanism for picking up the micro sample and hence, the micro sample thus picked up may be carefully corrected for its orientation with high precisions. Therefore, it is ensured that the picked micro sample is placed in a desired orientation. Furthermore, the invention is highly effective in the lift-out method permitting the additional processing. In the case of the lift-out method, the exact positioning of the micro sample is prerequisite because the placement of the micro sample must be carried out in a state where the micro sample is erected on the special sample stage. The conventional microscope system with manipulator does not provide for a precise correction of the orientation of the micro sample and hence, human mistakes are likely to occur. In contrast, the invention utilizes the low-vibration rotary mechanism incorporated in the micro-sample pick-up apparatus, thus offering the ability to correct the orientation of the micro sample with high precisions. Consequently, it is ensured that the micro sample is placed precisely.

What is claimed is:

1. A micro-sample pick-up apparatus for picking up a micro sample cut out from a sample and provided in a microscope system, the micro-sample pick-up apparatus comprising:

a probe for picking up the sample;

a probe holder for holding the probe;

an XYZ driver mechanism for moving the probe holder in the three-dimensional directions of X, Y and Z;

an observation mechanism for observing the sample and the probe; and a low-vibration rotary mechanism disposed in the probe holder for rotating the probe about an axis of the probe.

2. A micro-sample pick-up apparatus according to claim 1; wherein the observation mechanism is an optical microscope.

3. A micro-sample pick-up apparatus according to claim 1; wherein the observation mechanism is an electron microscope or an ion microscope.

4. A micro-sample pick-up apparatus comprising:
a probe for picking up a micro sample;
a probe holder for holding the probe so that the probe extends from a tip of the probe holder;
a driver mechanism for moving the probe holder in three-dimensional directions; and
rotary means for rotating the probe about a longitudinal axis thereof by rotating only the tip of the probe holder.

5. A micro-sample pick-up apparatus according to claim 4; further comprising an observation mechanism for observing the micro sample and the probe.

6. A micro-sample pick-up apparatus according to claim 5; wherein the observation mechanism comprises an optical microscope.

7. A micro-sample pick-up apparatus according to claim 5; wherein the observation mechanism comprises an electron microscope.

8. A micro-sample pick-up apparatus according to claim 5; wherein the observation mechanism comprises an ion microscope.

9. A micro-sample pick-up apparatus according to claim 4; wherein the rotary means is disposed in the probe holder.

10. A micro-sample pick-up apparatus according to claim 4; wherein the rotary means comprises a low-vibration rotary mechanism.

11. A micro-sample pick-up apparatus according to claim 10; wherein the low-vibration rotary mechanism is disposed in the probe holder.

12. A micro-sample pick-up apparatus for picking up a micro sample and correcting a rotational direction of the micro sample, the micro-sample pick-up apparatus comprising:
a probe for picking up a micro sample;
a probe holder for holding the probe so that the probe extends from a tip of the probe holder;
a driver mechanism for moving the probe holder in three-dimensional directions; and
rotary means for rotating the probe about a longitudinal axis thereof by rotating only the tip of the probe holder to thereby correct a rotational direction of the micro sample without substantially vibrating the micro sample.

13. A micro-sample pick-up apparatus according to claim 12; further comprising an observation mechanism for observing the micro sample and the probe.

14. A micro-sample pick-up apparatus according to claim 13; wherein the observation mechanism comprises an optical microscope.

15. A micro-sample pick-up apparatus according to claim 13; wherein the observation mechanism comprises an electron microscope.

16. A micro-sample pick-up apparatus according to claim 13; wherein the observation mechanism comprises an ion microscope.

17. A micro-sample pick-up apparatus according to claim 12; wherein the rotary means is disposed in the probe holder.

18. A micro-sample pick-up apparatus according to claim 12; wherein the rotary means comprises a low-vibration rotary mechanism.

19. A micro-sample pick-up apparatus according to claim 18; wherein the low-vibration rotary mechanism is disposed in the probe holder.

* * * * *